（12) United States Patent
Vicario et al.

(10) Patent No.: US 11,351,320 B2
(45) Date of Patent: Jun. 7, 2022

(54) AUTOMATIC PEEP SELECTION FOR MECHANICAL VENTILATION

(71) Applicant: KONINKLIJKE PHILIPS N.V., Eindhoven (NL)

(72) Inventors: Francesco Vicario, Boston, MA (US); Robert Buizza, Cambridge, MA (US); William Anthony Truschel, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 496 days.

(21) Appl. No.: 16/487,446

(22) PCT Filed: Feb. 22, 2018

(86) PCT No.: PCT/EP2018/054352
§ 371 (c)(1),
(2) Date: Aug. 21, 2019

(87) PCT Pub. No.: WO2018/153964
PCT Pub. Date: Aug. 30, 2018

(65) Prior Publication Data
US 2019/0374733 A1    Dec. 12, 2019

Related U.S. Application Data

(60) Provisional application No. 62/461,825, filed on Feb. 22, 2017.

(51) Int. Cl.
*A61M 16/00* (2006.01)
(52) U.S. Cl.
CPC ... *A61M 16/024* (2017.08); *A61M 2016/0027* (2013.01); *A61M 2016/0033* (2013.01);
(Continued)

(58) Field of Classification Search
CPC .............. A61M 16/021; A61M 16/022; A61M 16/024; A61M 16/026; A61M 16/0069; A61M 16/0057; A61M 16/009
See application file for complete search history.

(56) References Cited

U.S. PATENT DOCUMENTS 5,575,283 A    11/1996   Sjoestrand
6,709,405 B2    3/2004   Jonson
(Continued)

FOREIGN PATENT DOCUMENTS

EP         2397074 A1     12/2011
WO    WO2016189069 A1     12/2016

OTHER PUBLICATIONS

PCT International Search Report, International application No. PCT/EP2018/054352, dated Jun. 7, 2018.

*Primary Examiner* — Margaret M Luarca
(74) *Attorney, Agent, or Firm* — Daniel H. Brean

(57) ABSTRACT

The present disclosure pertains to a system (10) configured to automatically set the positive end expiratory pressure (PEEP) during mechanical ventilation (800). The system uses a measured relationship between transpulmonary pressure and lung volume (804) to set PEEP (808) such that mechanically assisted breaths are delivered more effectively to open airways (e.g., tidal breaths will be delivered to airways that consist of alveoli that have not contracted or collapsed at the end of expiration) (810). Furthermore, the system is configured to sense (18, 804) when the lungs may be either hyperextended and/or undergoing cyclic atelectasis in order to prevent trauma or injury to the lung's fibrous tissue. The system is configured to perform recruitment and/or continuous monitoring and adjustment of the PEEP setting to maintain an open lung.

13 Claims, 5 Drawing Sheets

(52) U.S. Cl.
CPC ............. *A61M 2205/3334* (2013.01); *A61M 2205/3344* (2013.01); *A61M 2230/46* (2013.01)

(56) References Cited

U.S. PATENT DOCUMENTS

| | | |
|---|---|---|
| 7,802,571 B2 | 9/2010 | Tehrani |
| 8,408,203 B2 | 4/2013 | Tham |
| 8,469,027 B2 | 6/2013 | Choncholas |
| 8,528,553 B2 | 9/2013 | Wysocki |
| 8,640,699 B2 | 2/2014 | Baker, Jr. |
| 2001/0051799 A1 | 12/2001 | Ingenito |
| 2009/0241946 A1 | 10/2009 | Baker, Jr. |
| 2010/0228142 A1 | 9/2010 | Sinderby |
| 2012/0167884 A1 | 7/2012 | Cardelius |
| 2015/0217069 A1 | 8/2015 | Novotni |
| 2016/0008561 A1 | 1/2016 | Novotni |
| 2018/0140793 A1* | 5/2018 | Stenqvist ............ A61M 16/024 |

* cited by examiner

AUTOMATIC PEEP SELECTION FOR MECHANICAL VENTILATION

CROSS-REFERENCE TO RELATED APPLICATIONS

This patent application claims the priority benefit under 35 U.S.C. § 371 of international patent application no. PCT/EP2018/050799, filed Jan. 15, 2018, which claims the priority benefit under 35 U.S.C. § 119(e) of U.S. Provisional Application No. 62/461,825 filed on Feb. 22, 2017, the contents of which are herein incorporated by reference.

BACKGROUND OF THE INVENTION

1. Field of the Invention

The present disclosure pertains to a method and a mechanical ventilator system for and controlling positive end expiratory pressure (PEEP) for a subject.

2. Description of the Related Art

A mechanical ventilator assists breathing by pushing air into a patient's lungs. Ventilators may operate under different control modes. Methods to dynamically and automatically combine recruitment maneuvers with the proper selection and maintenance of PEEP require static observations of lung volume with applied pressure. These methods are cumbersome and do not assess alveolar recruitment in real time, therefore requiring continual observation of the patient to prevent over distention, atelectasis or cyclic shearing of the alveoli.

SUMMARY OF THE INVENTION

Accordingly, one or more aspects of the present disclosure relate to a mechanical ventilator system configured to control positive end expiratory pressure (PEEP) in a subject. The mechanical ventilator system comprises a pressure generator, one or more sensors, one or more hardware processors, and/or other components. The pressure generator is configured to generate a pressurized flow of breathable gas for delivery to an airway of the subject. The one or more sensors are configured to generate output signals conveying information related to breathing of the subject. The one or more hardware processors are operatively coupled to the pressure generator and the one or more sensors and configured by machine-readable instructions to: determine tidal volume and transpulmonary pressure of the subject based on the information in the output signals; determine lung volume based on the tidal volume; determine a target PEEP level based on the lung volume and the transpulmonary pressure; and cause the pressure generator to adjust the pressurized flow of breathable gas to maintain the determined target PEEP level.

Another aspect of the present disclosure relates to a method for controlling PEEP in a subject with a mechanical ventilator system. The mechanical ventilator system comprises a pressure generator, one or more sensors, one or more hardware processors, and/or other components. The method comprises: generating, with the pressure generator, a pressurized flow of breathable gas for delivery to an airway of the subject; generating, with the one or more sensors, output signals conveying information related to breathing of the subject; determining, with the one or more hardware processors, tidal volume and transpulmonary pressure of the subject based on the information in the output signals; determining, with the one or more hardware processors, lung volume based on the tidal volume; determining, with the one or more hardware processors, a target PEEP level based on the lung volume and the transpulmonary pressure; and causing, with the one or more hardware processors, the pressure generator to adjust the pressurized flow of breathable gas to maintain the determined target PEEP level.

Still another aspect of the present disclosure relates to a system for controlling PEEP in a subject. The system comprises: means for generating a pressurized flow of breathable gas for delivery to an airway of the subject; means for generating output signals conveying information related to breathing of the subject; means for determining tidal volume and transpulmonary pressure of the subject based on the information in the output signals; means for determining, with the one or more hardware processors, lung volume based on the tidal volume; means for determining a target PEEP level based on the lung volume and the transpulmonary pressure; and means for causing the means for generating the pressurized flow of breathable gas to adjust the pressurized flow of breathable gas to maintain the determined target PEEP level.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
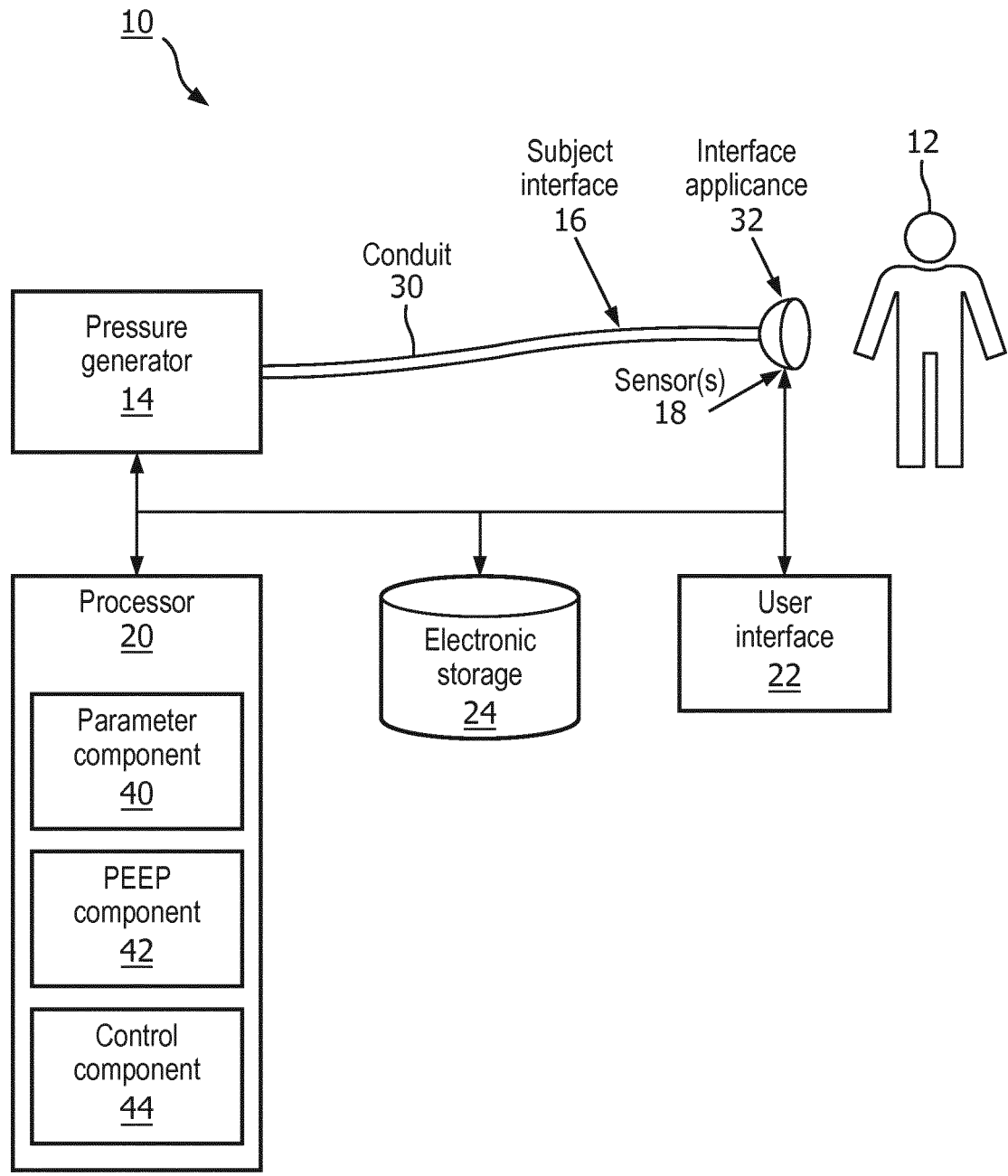
FIG. 1 is a schematic illustration of a system configured to control positive end expiratory pressure (PEEP) in a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a mechanical ventilator system 10 configured to control positive end expiratory pressure (PEEP) in a subject 12. In some embodiments, controlling PEEP includes selecting and maintaining target PEEP levels in subject 12. Collapsed lungs require applied pressure to expand alveoli. Once an alveolus is open, the alveolus tends to interact with neighboring alveoli and remain open. Recruitment maneuvers are used to open collapsed lungs and improve mechanical ventilation in subjects with respiratory difficulties. PEEP is controlled during recruitment maneuvers and/or at other times to prevent cyclic collapse as part of an open lung approach to ventilation in order to increase end-expiratory lung volume, improve gas exchange, decrease ventilator-induced lung injury (VILI), and/or for other reasons. Recruitment maneuvers include a temporary increase in airway pressure configured to open up collapsed alveoli. De-recruitment can occur, for instance, due to poor ventilation, insufficient PEEP, and/or chest wall instability, for example. Collapsed alveoli may lead to poor gas exchange and increased risk of VILI. Some alveoli may collapse during a breath, cyclically collapse and re-expand with individual breaths, and/or collapse at other times. At the same time, other alveoli in the lungs may remain inflated and/or become over inflated by high tidal volumes and pressures, causing volutrauma. Recruitment maneuvers may be used in subjects with severe acute respiratory distress syndrome (ARDS) and/or other subjects, may be a component of a lung protective ventilation strategy, and/or they may be used as part of an open lung approach to mechanical ventilation for example.

System 10 is configured to dynamically and automatically select and maintain a target PEEP level for and/or during recruitment maneuvers. Prior methods require static observations of subject lung volume and applied pressure. These prior methods are cumbersome and do not continue to assess alveolar recruitment in real time, therefore requiring continual observation of a subject to prevent over distention, atelectasis or cyclic shearing of the alveoli. As a subject in acute respiratory distress evolves, periodic recruitment maneuvers are occasionally needed to maintain an open lung. The target PEEP level needed during these maneuvers may vary over time (e.g., caused by surfactant treatment, the natural production of the lipids contained in surfactant to decrease the surface tension in the alveoli, and/or other factors). The varying need to assess and adjust a target PEEP level is a heavy burden on any caregiver during the administration of mechanical ventilation.

Existing tools available to caregivers to maintain an open lung are inadequate. For example, the pressure/volume (p-v) loops produced by typical ventilator systems plot tidal volume against mouth pressure. Such loops confound information pertaining to the alveoli by not taking into account the resistive pressure drop across the airways of a subject and subject (e.g., muscular) effort that contributes to the transmural pressure impacting the alveoli. As a consequence, the p-v loops need to be interpreted by a caregiver and, typically, static maneuvers by the caregiver (e.g., manually increasing pressure and observing the resulting tidal volume) are necessary to characterize the p-v relationship of the lung itself. Manually performed recruitment maneuvers require the presence of skilled personnel. As a consequence, such maneuvers are performed infrequently. The lack of continuous monitoring of PEEP further exacerbates the problem of infrequent recruitment maneuvers.

Advantageously, system 10 is configured to determine a target PEEP level based on a p-v curve with lung volume plotted against the transpulmonary pressure (i.e., the difference in pressure across the elastic compartment of the respiratory system (lung and chest wall)). Performing a recruitment maneuver typically involves high pressures in the lungs. System 10 is configured to monitor the alveolar (and, in turn, transpulmonary) pressure, rather than mouth pressure, and ensure it is maintained within safe limits.

System 10 is configured to determine the p-v curve (lung volume vs. transpulmonary pressure) in real-time and/or near real-time to facilitate automatic lung recruitment with a target PEEP level set and maintained throughout mechanical ventilation. System 10 is configured to help caregivers in their daily management of subjects by eliminating the need for performing manual recruitment maneuvers, among other advantages. System 10 is also useful during, for example, catastrophic events where a large number of people may need ventilation in the absence of skilled caregivers.

In some embodiments, system 10 comprises one or more of a pressure generator 14, a subject interface 16, one or more sensors 18, one or more processors 20, a user interface 22, electronic storage 24, and/or other components.

Pressure generator 14 is configured to generate a pressurized flow of breathable gas for delivery to the airway of subject 12. Pressure generator 14 may control one or more ventilation parameters of the flow of gas (e.g., rates, pressures, volumes, temperatures, compositions, etc.) for therapeutic purposes, and/or for other purposes. Pressure generator 14 is configured to control one or more ventilation parameters of the pressurized flow of breathable gas according to a prescribed mechanical ventilation therapy regime and/or other therapy regimes. By way of a non-limiting example, pressure generator 14 may be configured to control a breath rate, a flow rate, a mouth pressure waveform, a positive end expiratory pressure (PEEP), a tidal volume, a minute volume, an inspiratory to expiratory breath phase ratio (e.g., an I:E ratio), and/or other ventilation parameters of the flow of gas.

Pressure generator 14 receives a flow of gas from a gas source, such as the ambient atmosphere, and elevates and/or reduces the pressure of that gas for delivery to the airway of subject 12. Pressure generator 14 is and/or includes any device, such as, for example, a pump, blower, piston, or bellows, that is capable of elevating and/or reducing the pressure of the received gas for delivery to a patient. Pressure generator 14 may comprise servo controlled valves and/or motors, one or more other valves and/or motors for controlling the pressure and/or flow of gas, and/or other components. The present disclosure also contemplates controlling the operating speed of the blower, either alone or in combination with such valves, to control the pressure and/or flow of gas provided to subject 12.

Subject interface 16 is configured to deliver the pressurized flow of breathable gas to the airway of subject 12. As such, subject interface 16 comprises conduit 30, interface appliance 32, and/or other components. Conduit 30 is configured to convey the pressurized flow of gas to interface appliance 32. Conduit 30 may be a flexible length of hose, or other conduit that places interface appliance 32 in fluid communication with pressure generator 14. Interface appliance 32 is configured to deliver the flow of gas to the airway of subject 12. In some embodiments, interface appliance 32 is non-invasive. As such, interface appliance 32 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances.

Sensors 18 are configured to generate output signals conveying information related to breathing of subject 12 and/or other gas and/or breathing parameters. In some embodiments, the information related to breathing of subject 12 includes the flow rate (and/or information related to the flow rate) of the pressurized flow of breathable gas, pressure of the pressurized flow of breathable gas at the mouth of subject 12 and/or other locations, and/or other information. In some embodiments, the information related to breathing of subject 12 may comprise information related to volumes (e.g., tidal volume, minute volume, etc.), pressures (e.g., inhalation pressure, exhalation pressure, etc.), compositions (e.g., concentration(s)) of one or more constituent gasses, a gas temperature, a gas humidity, acceleration, velocity, acoustics, changes in a parameter indicative of respiratory effort by subject 12, and/or other parameters. In some embodiments, sensors 18 may generate output signals substantially continuously, at predetermined intervals, responsive to occurrence of a predetermined event, and/or at other times. In some embodiments, the predetermined intervals, events, and/or other information may be determined at manufacture, based on user input via user interface 22, and/or based on other information.

Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters).

Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, in communication with subject 12, and/or in other locations. For example, sensors 18 may include a flow rate sensor, a pressure sensor conveying information related a pressure of breathable gas at the mouth of subject 12 and/or other locations, a volume sensor, a temperature sensor, an acoustic sensor, a gas composition (e.g., an $SpO_2$ sensor) sensor, and/or other sensors located at various locations in system 10.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program components. The one or more computer program components may comprise one or more of a parameter component 40, a PEEP component 42, a control component 44, and/or other components. Processor 20 may be configured to execute components 40, 42, and/or 44 by software; hardware; firmware; some combination of software, hardware, and/or firmware; and/or other mechanisms for configuring processing capabilities on processor 20. In some embodiments, processor 20 may execute one or more of the operations described below and/or other operations substantially continuously (e.g., in real-time and/or near real-time), at predetermined intervals, responsive to occurrence of a predetermined event, and/or at other times. In some embodiments, the predetermined intervals, events, and/or other information may be determined at manufacture, based on user input via user interface 22, and/or based on other information.

It should be appreciated that although components 40, 42, and 44 are illustrated in FIG. 1 as being co-located within a single processing unit, in implementations in which processor 20 comprises multiple processing units, one or more of components 40, 42, and/or 44 may be located remotely from the other components. The description of the functionality provided by the different components 40, 42, and/or 44 described below is for illustrative purposes, and is not intended to be limiting, as any of components 40, 42, and/or 44 may provide more or less functionality than is described. For example, one or more of components 40, 42, and/or 44 may be eliminated, and some or all of its functionality may be provided by other components 40, 42, and/or 44. As another example, processor 20 may be configured to execute one or more additional components that may perform some or all of the functionality attributed below to one of components 40, 42, and/or 44.

Parameter component 40 is configured to determine tidal volume, lung volume, transpulmonary pressure, PEEP, and/or other parameters related to the pressurized flow of breathable gas and/or the breathing of subject 12. In some embodiments, the tidal volume, lung volume, the transpulmonary pressure, PEEP, and/or other parameters are determined based on the information in the output signals, determinations of one or more other parameters, and/or other information. For example, lung volume may be determined based on tidal volume by stitching together several measurements of tidal volume. In some embodiments, the information related to the breathing of subject 12 (e.g., the information in the output signals) includes a flow rate of the pressurized flow of breathable gas (Q), a pressure of breathable gas at a mouth of the subject ($P_{ao}$), and/or other information. In some embodiments, determining the tidal volume for subject 12 based on the information in the output signals comprises multiplying the flow rate by a period of time that corresponds to a given breath. In some embodiments, determining the transpulmonary pressure of subject 12 based on the information in the output signals comprises determining an airway resistance (R) and elasticity (E) based on Q and $P_{ao}$, determining alveolar pressure ($P_{al}$) and muscular pressure ($P_{mus}$) in subject 12 based on R and E, and determining the transpulmonary pressure based on $P_{al}$ and $P_{mus}$.

Figure 2:
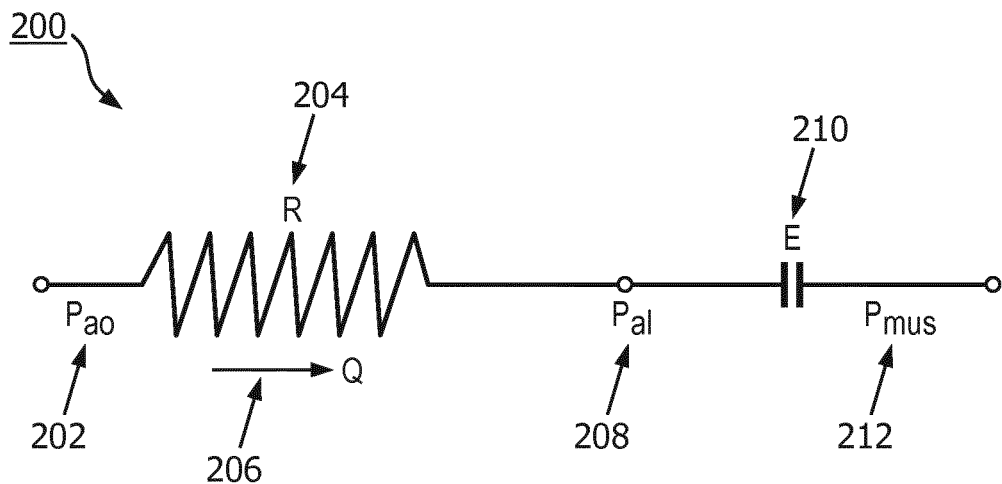
FIG. 2 schematically illustrates $P_{ao}$, R, Q, $P_{al}$, E, and $P_{mus}$ in the respiratory mechanics system represented as a single compartment linear model.

FIG. 2 schematically illustrates how the above parameters are dynamically related to each other. The patient's respiratory system is modeled as a single compartment, represented in FIG. 2 as an electrical analogue 200. The lungs and chest wall are modeled as an elastic compartment served by a single resistive pathway (airways). The pressure at the entrance of the resistive pathway corresponds to the airway opening pressure ($P_{ao}$ 202), whereas the pressure inside the elastic compartment is representative of the alveolar pressure ($P_{al}$ 208). The system is subject to an external pressure ($P_{mus}$ 212) that represents an equivalent pressure of the force exerted by the respiratory muscles. The dynamics of the airflow Q through the different components of the respiratory system is driven by the pressure difference $P_{ao}-P_{mus}$. The elastic properties of the elastic compartment are described by the elastance parameter E 210 and the resistive properties of the resistive component are described by the resistance parameter R 204.

Using the model shown in FIG. 2, the transpulmonary pressure, or the pressure across the elastic compartment of the respiratory system, can be determined by subtracting $P_{mus}$ from $P_{al}$, where the elastic element E 210 includes both the lungs and the chest wall. Determining a resistance (R) and elasticity (E) based on Q and $P_{ao}$ (e.g., determined based on the information in the output signals from sensors 18) may be performed according to the equation(s) shown below and/or other equations. For example:

$$\tau = \text{median}(-(V(t)-V(t_0))/(Q(t)-Q(t_0))),$$

over the time samples t during exhalation at which the ventilator is providing the set PEEP. Also:

$$E=(Pao(tEOI)-Pao(t0))/(\tau(Q(tEOI)-Q(t0))+(V(tEOI)-V(t0))); \text{ and}$$

$$R=\tau E,$$

where $t_0$ is the time at which the patient initiates the breath (or the ventilator does, if the patient is passive) and $t_{EOI}$ is the time at which the ventilator cycles off. $\tau$ is the respiratory system time constant, which can be estimated as a median (like above) or, for instance, by the ordinary least-squares method. Determining alveolar pressure ($P_{al}$) and muscular pressure ($P_{mus}$) in subject 12 based on R and E may be performed according to the equation(s) shown below and/or other equations. For example:

$$Pal(t)=Pao(t)-RQ(t); \text{ and}$$

$$Pmus(t)=Pao(t)-RQ(t)-E(V(t)-(V(t0))-Pal(t0).$$

As described above, determining the transpulmonary pressure $P_{transpulmonary}$ based on $P_{al}$ and $P_{mus}$ may be performed according to the equation shown below and/or other equations.

$$Ptranspulmonary(t)=Pal(t)-Pmus(t)$$

Figure 3:
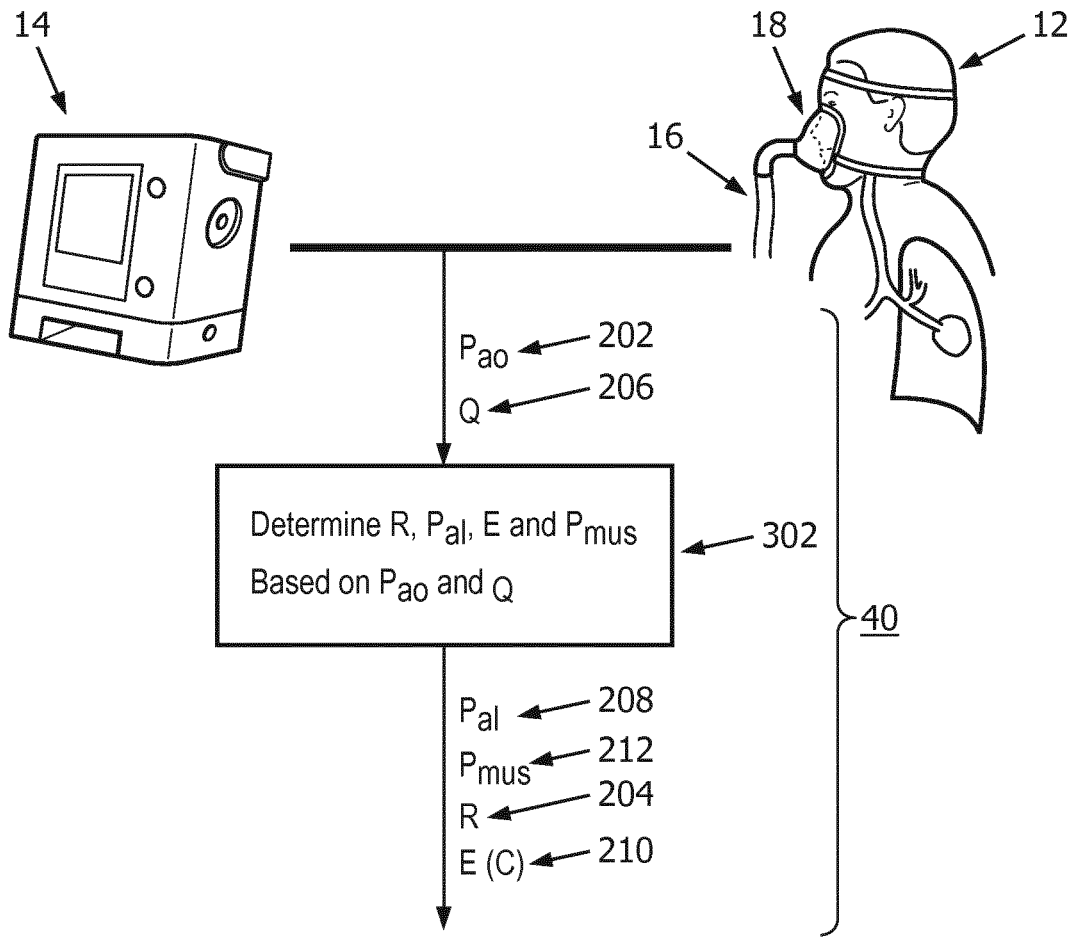
FIG. 3 illustrates an input-output diagram showing determination of parameters R, $P_{al}$, E, and $P_{mus}$ based on $P_{ao}$ and Q.

By way of a non-limiting example, FIG. 3 is an input-output diagram 300 showing determination 302 (e.g., using the equations described above) of parameters R 204, $P_{al}$ 208, E 210, and $P_{mus}$ 212 based on $P_{ao}$ 202 and Q 206. As shown in FIG. 3, system 10 (FIG. 1) is configured such that only air flow (Q 206) and pressure ($P_{ao}$ 202) measurements made based on information in output signals from sensors 18 located in communication with subject interface 16 at the mouth of subject 12 are needed to make breath by breath estimates of R 204, E 210, $P_{at}$ 208, $P_{mus}$ 212, and/or other parameters. In some embodiments (e.g., during non-invasive ventilation), flow and pressure at the mouth of the subject are estimated based on flow and pressure measurements obtained with sensors located in the ventilator.

In some embodiments, transmural pressure ($P_{at}$—pleural pressure ($P_{pl}$)) is determined instead of and/or in addition to transpulmonary pressure, and the target PEEP level is determined (e.g., as described herein) based on the lung volume, the transmural pressure, and/or other information. In such embodiments, subject interface 16 (FIG. 1) and/or sensors 18 (FIG. 1) may include one or more invasive components configured to facilitate measurement of pleural pressure (e.g., via an esophageal catheter and/or other components).

Returning to FIG. 1, PEEP component 42 is configured to determine a target PEEP level. The target PEEP level is determined based on the information in the output signals from sensors 18, the parameters determined by parameter component 40 (e.g., including the lung volume, the transpulmonary pressure, and/or other parameters), and/or other information. In some embodiments, PEEP component 42 is configured to determine a target PEEP level by controlling pressure generator 14 to generate the pressurized flow of breathable gas to achieve a series of increasing PEEP levels in subject 12 over a series of breaths by subject 12 and determining airway compliance C (e.g., 1/E described above) for the individual PEEP levels. In some embodiments, PEEP component 42 is configured such that the breaths with increasing PEEP levels are tidal volume controlled and/or alveolar pressure limited during breathing to ensure safety of subject 12 (e.g., wherein the necessary safety determinations are made based on the information in the output signals from sensors 18, based on limitations and/or other entries and/or selections made via user interface 22, and/or based on other information). A tidal volume controlled and alveolar pressure limited breath is a breath delivered with pressure support or ramping pressure until the inhaled volume reaches the volume threshold given by a prescription, for example.

Figure 4:
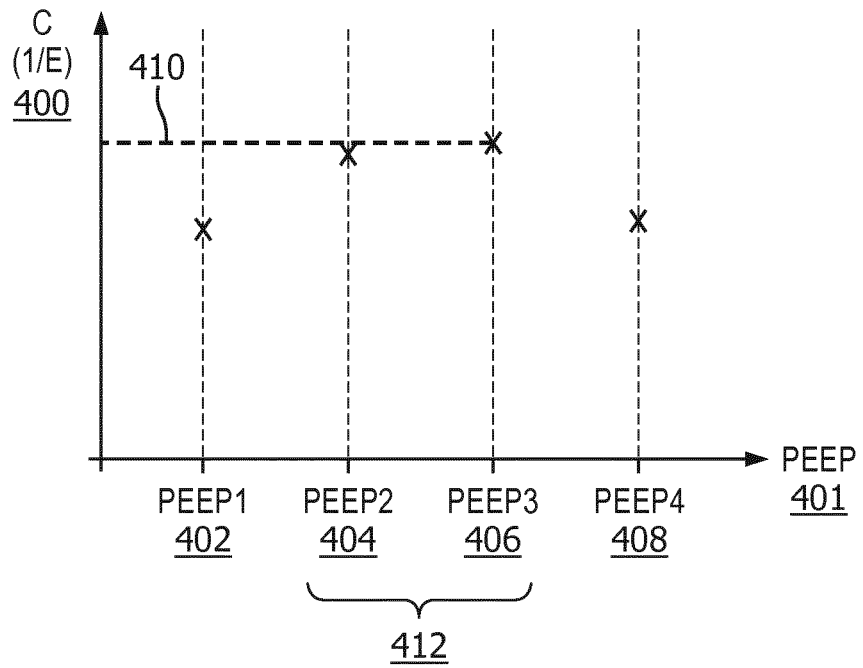
FIG. 4 illustrates airway compliance as a function if increasing PEEP levels.

FIG. 4 illustrates airway compliance C 400 as a function if increasing PEEP 401 levels 402, 404, 406, and 408. In such embodiments, based on the compliance versus PEEP information (e.g., the information in FIG. 4), PEEP component 42 (FIG. 1) is configured to set the target PEEP level at or near PEEP levels that generate maximum or near-maximum lung compliance in subject 12 (FIG. 1). Using FIG. 4 as an example, maximum lung compliance (or minimum elastance) 410 is achieved at or near PEEP levels 404 and 406 so PEEP component 42 would set the target PEEP level 412 to a level at or near PEEP levels 404 and/or 406.

Figure 5:
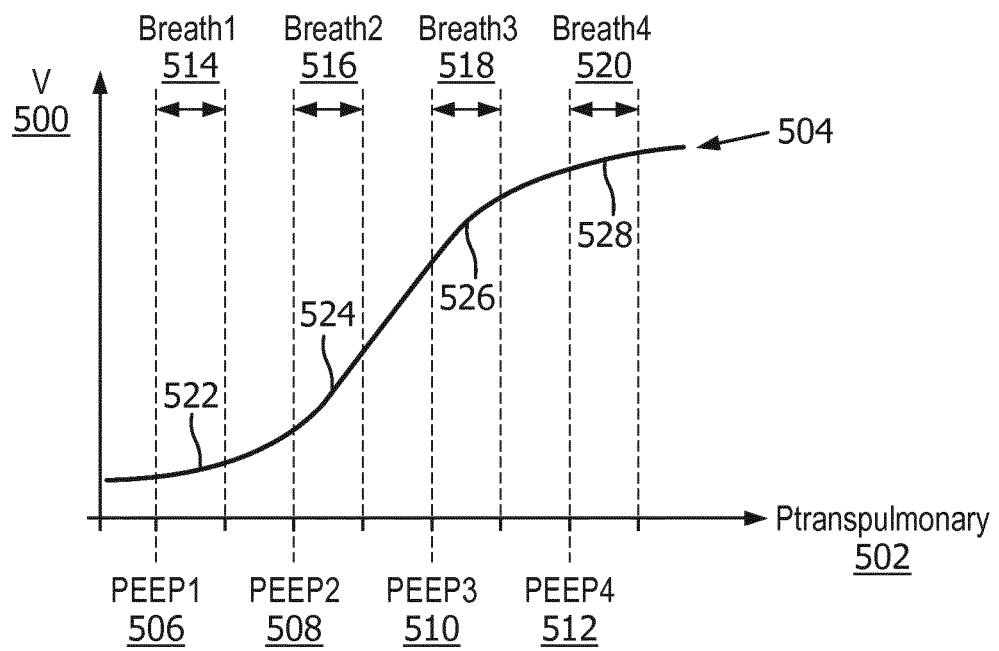
FIG. 5 illustrates an example p-v curve for the lungs of the subject.

In some embodiments, determining the target PEEP level based on the lung volume and the transpulmonary pressure comprises determining a lung volume (e.g., by stitching together several measurements of tidal volume) versus transpulmonary pressure (e.g., determined as described above) curve based on the information in the output signals, parameters determined by parameter component 40 (FIG. 1), and/or other information. In some embodiments, the lung volume portion of the curve is generated by stitching together many measurements of tidal volume and offsetting them by the start volume at the beginning of the breath, and/or by other methods. FIG. 5 illustrates an example of a lung volume (V) 500 versus transpulmonary pressure ($P_{transpulmonary}$) 502 curve 504 for subject 12 (FIG. 1). In some embodiments, PEEP component 42 (FIG. 1) is configured to determine curve 504 by controlling pressure generator 14 (FIG. 1) to generate the pressurized flow of breathable gas to achieve a series of increasing PEEP levels 506, 508, 510, and 512 in subject 12 over a series of breaths 514, 516, 518, and 520 by subject 12 and plotting the resulting lung volume versus transpulmonary pressure (e.g., determined as described above) for the individual breaths 514-520. As shown in FIG. 5, information generated for the individual breaths 514-520 is used to determine corresponding portions 522-528 of curve 504.

A transpulmonary pressure p-v curve of the lungs of subject 12 (FIG. 1) features three main regions. At low pressure, the curve is generally flat (e.g., large changes in pressure are needed to achieve relatively small changes in volume). This corresponds to low lung compliance. A central region of the curve is characterized by higher lung compliance and corresponds to a pressure range within which the lungs operate at their best, without alveolar collapse or overstretching. At higher pressures, the p-v curve becomes flat as again large changes in pressure are needed to achieve relatively small changes in volume.

Figure 6:
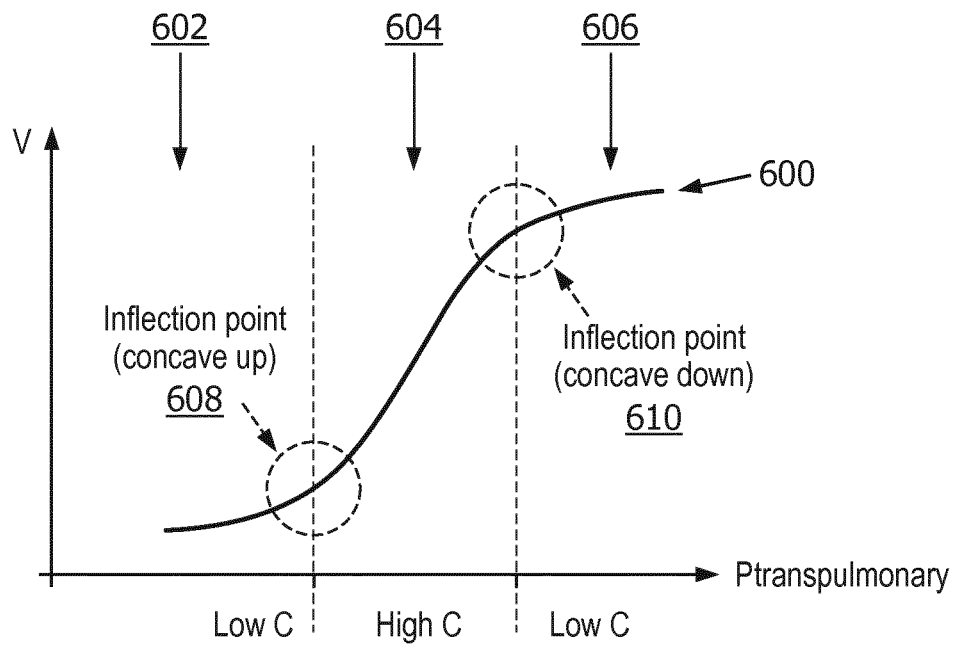
FIG. 6 illustrates another example p-v curve for the lungs of the subject.

FIG. 6 illustrates another example p (transpulmonary)-v (lung) curve 600 of the lungs of subject 12 (e.g., for simplicity hysteresis and/or interaction of the alveoli to maintain themselves once opened is not shown in FIG. 6). FIG. 6 illustrates a lower region 602 where, at low pressure, curve 600 is generally flat (e.g., large changes in pressure are needed to achieve relatively small changes in volume). FIG. 6 illustrates a central region 604 of curve 600 characterized by higher lung compliance, and a higher region 606 where, at higher pressures, p-v curve 600 becomes flat as again large changes in transpulmonary pressure are needed to achieve relatively small changes in volume. As shown in FIG. 6, region 602 transitions to region 604 at a concave up inflection point 608 in curve 600, and region 604 transitions to region 606 at a concave down inflection point 610 in curve 600. Also in FIG. 6, the $P_{transpulmonary}$ axis shows the pressure across the elastic compartment of the respiratory system (e.g., $P_{al}$-$P_{mus}$, where the elastic element includes both the lungs and the chest wall).

Returning to FIG. 1, in some embodiments, PEEP component 42 is configured such that determining the target PEEP level based on the lung volume and the transpulmonary pressure comprises identifying one or more inflection points (e.g., 608 and/or 610 shown in FIG. 6) in the p (transpulmonary)-v (lung) curve, determining the target PEEP level based on the one or more inflection points, and/or performing other operations. In some embodiments, PEEP component 42 determines inflection points in the p (transpulmonary)-v (lung) curve by, for instance, detecting changes in the value of the derivative of curve 600. In some embodiments, PEEP component 42 is configured such that the derivative can be computed locally (i.e., point by point, along curve 600) using a Savitzky-Golay smoothening filter, and/or other techniques.

In some embodiments, determining the target PEEP level based on the lung volume and the transpulmonary pressure further comprises identifying a concave up inflection point in the curve and/or causing pressure generator 14 to adjust the pressurized flow of breathable gas to increase therapy PEEP levels in subject 12 for individual breaths in a series of subsequent breaths until a concave up inflection point is no longer identified in a portion of the curve that corresponds to a most recent breath. In some embodiments, determining the target PEEP level based on the lung volume and the transpulmonary pressure further comprises identifying a concave down inflection point in the curve, causing pressure generator 14 to adjust the pressurized flow of breathable gas to decrease therapy PEEP levels in subject 12 for individual breaths in a series of subsequent breaths until a concave up inflection point is identified, causing pressure generator 14 to adjust the pressurized flow of breathable gas to increase therapy PEEP levels for at least one further breath to a level between the concave down inflection point and the concave up inflection point, and setting the target PEEP level to a level between a pressure that corresponds to the concave up inflection point and the therapy PEEP level for the at least one further breath to maintain an open airway in subject 12.

Figure 7:
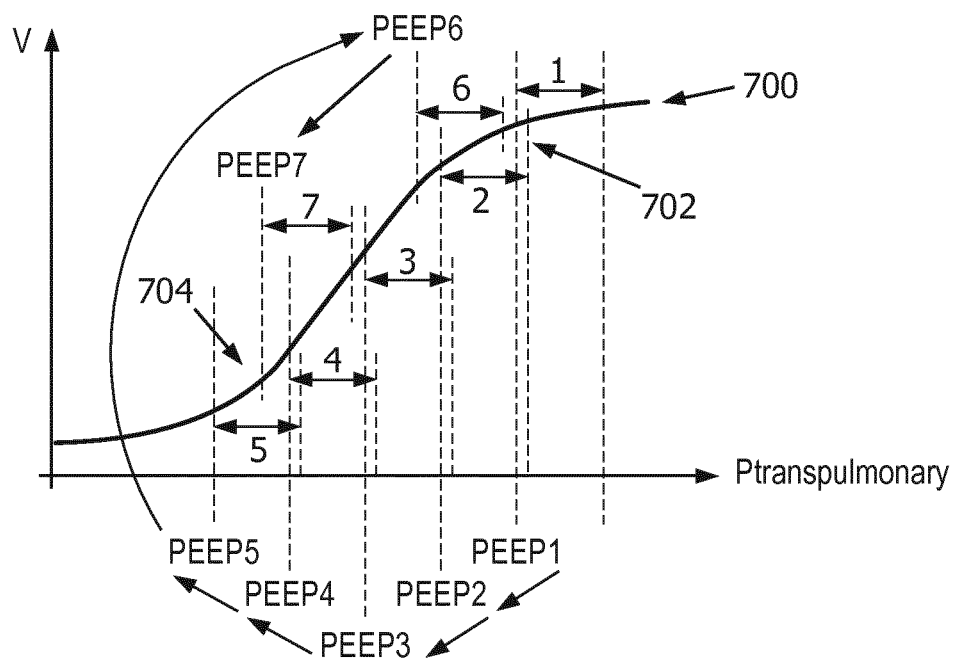
FIG. 7 illustrates one possible set of operations performed by the system to determine a target PEEP level.

For example, FIG. 7 illustrates one possible set of operations 700 performed by PEEP component 42 (FIG. 1) to determine a target PEEP level. As described above, PEEP component 42 may cause pressure generator 14 (FIG. 1) to generate the pressurized flow of breathable gas to achieve a series of PEEP levels (e.g., PEEP 1-PEEP 7) in subject 12 (FIG. 1) over a series of breaths (e.g., 1-7) by subject 12. FIG. 7 illustrates identifying a concave down inflection point in the curve 702, causing pressure generator 14 to adjust the pressurized flow of breathable gas to decrease therapy PEEP levels (e.g., PEEP 2-PEEP 5) in subject 12 for individual breaths (e.g., breaths 2-5) in a series of subsequent breaths until a concave up inflection point 704 is identified, causing pressure generator 14 to adjust the pressurized flow of breathable gas to increase therapy PEEP levels (e.g., PEEP 6) for at least one further breath (e.g., breath 6) to a level between concave down inflection point 702 and concave up inflection point 704, closer to 702, and eventually setting the target PEEP level to a level (e.g., PEEP 7) between concave down inflection point 702 and concave up inflection point 704, closer to 704, to maintain an open airway in subject 12.

Returning to FIG. 1, in some embodiments, PEEP component 42 is configured to perform one or more of the operations described above to determine a target PEEP level one or more times per breath of subject 12 such that target PEEP levels are determined in real-time and/or near real-time (e.g., such that a plot like the plot illustrated in FIG. 6 may be generated and/or updated for individual breaths of subject 12). In some embodiments, PEEP component 42 is configured to perform one or more of the operations described above responsive to detection of a concave up inflection point in a p (transpulmonary)-v (lung) curve. In some embodiments, PEEP component 42 is configured to perform one or more of the operations described above responsive to one or more parameters determined by parameter component 40 breaching a threshold level. For example, PEEP component 42 may be configured to perform one or more of the operations described above to determine a target PEEP level responsive to parameters indicating a low ventilation alarm condition (e.g., one or more parameters breaching a low ventilation alarm threshold), a SpO2 level breaching an SpO2 alarm threshold level, and/or responsive to other parameters breaching other thresholds. In some embodiments, PEEP component 42 is configured to perform one or more of the operations described above to determine a target PEEP level at predetermined intervals that may or may not correspond to the breathing of subject 12. In some embodiments, PEEP component 42 is configured to perform one or more of the operations described above to determine a target PEEP level responsive to manual instructions received from a user (e.g., via user entry and/or selection of such instructions via user interface 22 and/or other components of system 10). In some embodiments, the timing of the target PEEP level determinations (e.g., real-time, near real-time, responsive to threshold breach, at predetermined intervals, responsive to manual instructions, etc.) is set at manufacture, determined and/or adjusted based on user input via user interface 22, and/or determined by other methods.

Control component 44 is configured to control pressure generator 14 to generate the pressurized flow of breathable gas. The pressurized flow of gas generated by pressure generator 14 is controlled to replace and/or compliment the regular breathing of subject 12. In some embodiments, control component 44 is configured to cause pressure generator 14 to generate the pressurized flow of breathable gas in accordance with a prescribed mechanical ventilation therapy regime. In such embodiments, control component 44 is configured to cause pressure generator 14 to control the one or more ventilation parameters of the pressurized flow of breathable gas (e.g., as described above) according to the prescribed mechanical ventilation therapy regime. In some embodiments, control component 44 may be configured to control pressure generator 14 to generate the flow of gas in accordance with a ventilation and/or positive airway pressure support therapy regime in addition to and/or instead of a mechanical ventilation therapy regime. By way of non-limiting example, control component 44 may control pressure generator 14 such that the pressure support provided to subject 12 via the flow of gas comprises continuous positive airway pressure support (variable CPAP), variable bi-level positive airway pressure support (BPAP), proportional positive airway pressure support (PPAP), and/or other types of pressure support therapy.

In some embodiments, control component 44 is configured to cause pressure generator 14 to adjust the pressurized flow of breathable gas to provide the therapy PEEP levels describe herein (e.g., the adjusted PEEP levels described above used to determine target PEEP levels) and/or maintain a determined target PEEP level. Maintaining the determined target PEEP level may facilitate maintenance of an open airway in subject 12 so that oxygen and carbon dioxide may be exchanged more easily, requiring little and/or no effort from subject 12 in order to facilitate gas exchange. Control component 44 is configured to control pressure generator 14 based on information related to the output signals from sensors 18, information determined by PEEP component 42 and/or parameter component 40, information entered and/or selected by a user via user interface 22, and/or other information.

By way of a non-limiting practical example of the operation of components 40, 42, and/or 44 of processor 20 and/or other components of system 10 described herein, system 10 may deliver a recruitment maneuver (e.g., autonomously triggered by system 10 and/or manually triggered by an external user) comprising a series of increasing tidal volume controlled and alveolar pressure limited breaths (pressures) to subject 12, beginning at an initial PEEP of 15 $cmH_2O$, for example. As described above, tidal volume controlled and alveolar pressure limited breaths are breaths delivered with pressure support and/or ramping pressure until the inhaled volume reaches the volume threshold given by a prescription (e.g., 6 cc/kg ideal body weight (IBW) entered and/or selected via user interface 22 and/or other components of system 10) and/or until the alveolar pressure reaches 30 $cmH_2O$, as an example, after which the pressure is lowered back to the PEEP setting. System 10 may cause delivery one or more of these breaths in order to stabilize the parameter estimation algorithms described above, and/or build a robust estimate of a corresponding p (transpulmonary)-v (lung) curve segment (e.g., by averaging determinations from different breaths). If an inflection point with upward concavity is detected in the estimated p-v curve segment, then PEEP may be increased to a level of pressure corresponding to the inflection point plus 2 $cmH_2O$, for example. Further breaths may then be delivered at the new PEEP level while further breathing parameters continue to be determined and the above procedure is repeated until the determined segment of the p-v curve does not feature the lower inflection point (the concave up inflection point).

If a detected inflection point is concave down, then system 10 is configured such that the PEEP level setting is decreased by as many $cmH_2O$ as needed to move down the p-v curve and make the upper inflection point (the concave down inflection point) disappear for a given curve segment (e.g., segments 524 and 526 in FIG. 5). Afterwards, successive decreases in PEEP levels are made (while breaths are continually delivered) until the concave up inflection point appears. This level of PEEP corresponds to atelectasis and system 10 sets the target PEEP level above this pressure. The recruitment procedure (stepped increases in the PEEP level) is repeated, but is subsequently followed with a decrease in PEEP to a level 2 cm $H_2O$, for example, above the learned level of PEEP that caused atelectasis. It should be noted that atelectasis may be detected at any time by system 10 during the administration of mechanical ventilation via detection of the lower inflection point (the concave up inflection point). As described above, responsive to detection of a concave up inflection point by system 10 (e.g., PEEP component 42) and/or other events, system 10 (e.g., PEEP component 42 and/or pressure generator 14) is configured to perform a recruitment maneuver according to the procedure described herein.

User interface 22 is configured to provide an interface between system 10 and subject 12 and/or other users through which subject 12 and/or other users provide information to and receive information from system 10. Other users may comprise a caregiver, a doctor, a family member, a decision maker, and/or other users. User interface 22 enables data, cues, results, and/or instructions and any other communicable items, collectively referred to as "information," to be communicated between a user (e.g., subject 12) and one or more of pressure generator 14, sensors 18, processor 20, electronic storage 24, and/or other components of system 10. Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 22 comprises a plurality of separate interfaces. In some embodiments, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Figure 8:
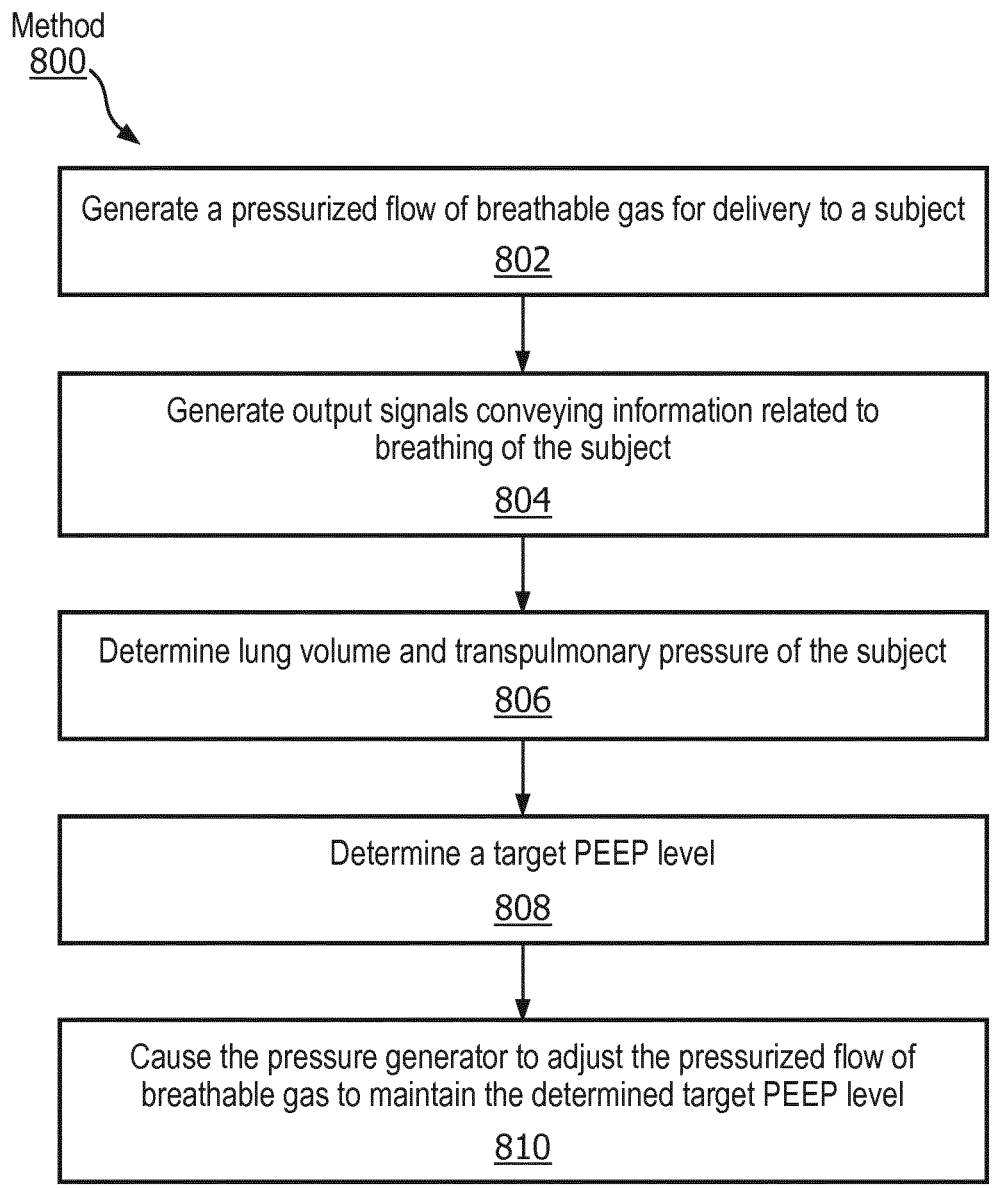
FIG. 8 illustrates a method for controlling PEEP in the subject.

FIG. 8 illustrates a method 800 for controlling PEEP in a subject with a mechanical ventilator system. The mechanical ventilator system comprises a pressure generator, one or more sensors, one or more hardware processors, and/or other components. The one or more hardware processors are configured by machine-readable instructions to execute computer program components. The computer program components include a parameter component, a PEEP component, a control component, and/or other components. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, a pressurized flow of breathable gas is generated for delivery to the airway of the subject. In some embodiments, operation 802 is performed by a pressure generator the same as or similar to pressure generator 14 (shown in FIG. 1 and described herein).

At an operation 804, output signals conveying information related to breathing of the subject are generated. In some embodiments, operation 804 is performed by one or more sensors the same as or similar to sensors 18 (shown in FIG. 1 and described herein). In some embodiments, the one or more sensors comprise a flow rate sensor configured to generate output signals conveying information related to a flow rate of the pressurized flow of breathable gas, a pressure sensor conveying information related a pressure of breathable gas at a mouth of the subject, and/or other sensors.

At an operation 806, lung volume and transpulmonary pressure of the subject are determined. The lung volume and the transpulmonary pressure are determined based on the information in the output signals, based on one or more determined parameters (e.g., the lung volume may be determined based on tidal volume, the tidal volume determined based on the output signals; and the transpulmonary pressure may be determined based on the parameters and equations above), and/or other information. In some embodiments, the information related to the breathing of the subject includes a flow rate of the pressurized flow of breathable gas (Q), a pressure of breathable gas at a mouth of the subject ($P_{ao}$), and/or other information. In some embodiments, determining the transpulmonary pressure of the subject based on the information in the output signals comprises: determining an airway resistance (R) and elasticity (E) based on Q and $P_{ao}$; determining alveolar pressure ($P_{al}$) and muscular pressure ($P_{mus}$) in the subject based on R and E; and determining the transpulmonary pressure based on $P_{al}$ and $P_{mus}$. In some embodiments, transmural pressure is determined instead of transpulmonary pressure, and the target PEEP level is determined (e.g., as described herein) based on the lung volume, the transmural pressure, and/or other information. In some embodiments, operation 806 is performed by a processor component the same as or similar to parameter component 40 (shown in FIG. 1 and described herein).

At an operation 808, a target PEEP level is determined. The target PEEP level is determined based on the lung volume, the transpulmonary pressure, and/or other information. In some embodiments, determining the target PEEP level based on the lung volume and the transpulmonary pressure comprises: determining a lung volume versus transpulmonary pressure curve based on the information in the output signals, determined parameters, and/or other information; identifying one or more inflection points in the curve; and determining the target PEEP level based on the one or more inflection points. In some embodiments, determining the target PEEP level based on the lung volume and the transpulmonary pressure further comprises: identifying a concave down inflection point in the curve; causing the pressure generator to adjust the pressurized flow of breathable gas to decrease therapy PEEP levels in the subject for individual breaths in a series of subsequent breaths until a concave up inflection point is identified; causing the pressure generator to adjust the pressurized flow of breathable gas to increase therapy PEEP levels for at least one further breath to a level between the concave down inflection point and the concave up inflection point; and setting the target PEEP level to a level between a pressure that corresponds to the concave up inflection point and the therapy PEEP level for the at least one further breath to maintain an open airway in the subject. In some embodiments, determining the target PEEP level based on the lung volume and the transpulmonary pressure further comprises: identifying a concave up inflection point in the curve; and causing the pressure generator to adjust the pressurized flow of breathable gas to increase therapy PEEP levels in the subject for individual breaths in a series of subsequent breaths until the concave up inflection point is no longer identified in a portion of the curve that corresponds to a most recent breath. In some embodiments, operation 808 is performed by a processor component the same as or similar to PEEP component 42 (shown in FIG. 1 and described herein).

At an operation 810, the pressure generator is caused to adjust the pressurized flow of breathable gas to maintain the determined target PEEP level. In some embodiments, operation 810 is performed by a processor component the same as or similar to control component 44 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A mechanical ventilator system configured to control positive end expiratory pressure (PEEP) in a subject, the mechanical ventilator system comprising:
   a pressure generator configured to generate a pressurized flow of breathable gas for delivery to an airway of the subject;
   one or more sensors configured to generate output signals conveying information related to breathing of the subject, wherein the information related to the breathing of the subject includes a flow rate of the pressurized flow of breathable gas (Q) and a pressure of breathable gas at a mouth of the subject ($P_{ao}$); and
   one or more hardware processors operatively coupled to the pressure generator and the one or more sensors configured by machine-readable instructions to:
      determine tidal volume and transpulmonary pressure of the subject based on the information in the output signals, wherein determining the transpulmonary pressure of the subject based on the information in the output signals comprises:
         determining an airway resistance (R) and elasticity (E) based on Q and $P_{ao}$;
         determining alveolar pressure ($P_{al}$) and muscular pressure ($P_{mus}$) in the subject based on R and E; and
         determining the transpulmonary pressure based on $P_{al}$ and $P_{mus}$;
      determine a target PEEP level based on lung volume and the transpulmonary pressure, the lung volume determined based on the tidal volume; and
      cause the pressure generator to adjust the pressurized flow of breathable gas to maintain the determined target PEEP level.

2. The system of claim 1, wherein the one or more hardware processors are configured such that determining the target PEEP level based on the lung volume and the transpulmonary pressure comprises:
   determining a lung volume versus transpulmonary pressure curve based on the information in the output signals;
   identifying one or more inflection points in the curve; and
   determining the target PEEP level based on the one or more inflection points.

3. The system of claim 2, wherein the one or more hardware processors are configured such that determining the target PEEP level based on the lung volume and the transpulmonary pressure further comprises:
   identifying a concave down inflection point in the curve;
   causing the pressure generator to adjust the pressurized flow of breathable gas to decrease therapy PEEP levels in the subject for individual breaths in a series of subsequent breaths until a concave up inflection point is identified;
   causing the pressure generator to adjust the pressurized flow of breathable gas to increase therapy PEEP levels for at least one further breath to a level between the concave down inflection point and the concave up inflection point, to the concave down inflection point; and
   setting the target PEEP level, for at least one second further breath to maintain an open airway in the subject, to a level between a pressure that corresponds to the concave down inflection point and the concave up inflection point, close to the concave up inflection point.

4. The system of claim 2, wherein the one or more hardware processors are configured such that determining the target PEEP level based on the lung volume and the transpulmonary pressure further comprises:
   identifying a concave up inflection point in the curve; and
   causing the pressure generator to adjust the pressurized flow of breathable gas to increase therapy PEEP levels in the subject for individual breaths in a series of subsequent breaths until the concave up inflection point is no longer identified in a portion of the curve that corresponds to a most recent breath.

5. The system of claim 2, wherein the one or more hardware processors are further configured to:
   identify concave up and concave down inflection points in the curve; and
   automatically suggest a recruitment maneuver responsive to:
      a compliance reduction over time at a constant PEEP level, the compliance reduction over time determined based on the information in the output signals; and/or
      a change in position of the inflection points.

6. The system of claim 1, wherein the one or more sensors comprise a flow rate sensor configured to generate output signals conveying information related to a flow rate of the pressurized flow of breathable gas, and a pressure sensor conveying information related to a pressure of breathable gas at a mouth of the subject.

7. The system of claim 1, wherein the one or more hardware processors are further configured to determine transmural pressure, and determine the target PEEP level based on the lung volume and the transmural pressure.

8. A method for controlling positive end expiratory pressure (PEEP) in a subject with a mechanical ventilator system, the mechanical ventilator system comprising a pressure generator, one or more sensors, and one or more hardware processors, the method comprising:

generating, with the pressure generator, a pressurized flow of breathable gas for delivery to an airway of the subject;

generating, with the one or more sensors, output signals conveying information related to breathing of the subject, wherein the information related to the breathing of the subject includes a flow rate of the pressurized flow of breathable gas (Q) and a pressure of breathable gas at a mouth of the subject ($P_{ao}$);

determining, with the one or more hardware processors, tidal volume and transpulmonary pressure of the subject based on the information in the output signals wherein determining the transpulmonary pressure of the subject based on the information in the output signals comprises:

determining an airway resistance (R) and elasticity (E) based on Q and $P_{ao}$;

determining alveolar pressure ($P_{al}$) and muscular pressure ($P_{mus}$) in the subject based on R and E; and determining the transpulmonary pressure based on $P_{al}$ and $P_{mus}$;

determining, with the one or more hardware processors, a target PEEP level based on lung volume and the transpulmonary pressure, the lung volume determined based on the tidal volume; and causing, with the one or more hardware processors, the pressure generator to adjust the pressurized flow of breathable gas to maintain the determined target PEEP level.

9. The method of claim 8, wherein determining the target PEEP level based on the lung volume and the transpulmonary pressure comprises:

determining a lung volume versus transpulmonary pressure curve based on the information in the output signals;

identifying one or more inflection points in the curve; and determining the target PEEP level based on the one or more inflection points.

10. The method of claim 9, wherein determining the target PEEP level based on the lung volume and the transpulmonary pressure further comprises:

identifying a concave down inflection point in the curve;

causing the pressure generator to adjust the pressurized flow of breathable gas to decrease therapy PEEP levels in the subject for individual breaths in a series of subsequent breaths until a concave up inflection point is identified;

causing the pressure generator to adjust the pressurized flow of breathable gas to increase therapy PEEP levels for at least one further breath to a level between the concave down inflection point and the concave up inflection point, closer to the concave down inflection point; and setting the target PEEP level, for at least one second further breath to maintain an open airway in the subject, to a level between a pressure that corresponds to the concave down inflection point and the concave up inflection point, close to the concave up inflection point.

11. The method of claim 9, wherein determining the target PEEP level based on the lung volume and the transpulmonary pressure further comprises:

identifying a concave up inflection point in the curve; and causing the pressure generator to adjust the pressurized flow of breathable gas to increase therapy PEEP levels in the subject for individual breaths in a series of subsequent breaths until the concave up inflection point is no longer identified in a portion of the curve that corresponds to a most recent breath.

12. The method of claim 9, further comprising:

identifying concave up and concave down inflection points in the curve; and automatically suggesting a recruitment maneuver responsive to:

a compliance reduction over time at a constant PEEP level, the compliance reduction over time determined based on the information in the output signals; and/or a change in position of the inflection points.

13. The method of claim 8, wherein the one or more sensors comprise a flow rate sensor configured to generate output signals conveying information related to a flow rate of the pressurized flow of breathable gas, and a pressure sensor conveying information related to a pressure of breathable gas at a mouth of the subject.

* * * * *